United States Patent
Park et al.

(10) Patent No.: US 6,372,236 B1
(45) Date of Patent: Apr. 16, 2002

(54) CREAM COMPOSITION FOR SKIN CARE

(75) Inventors: Chang Seo Park, Kwachon; Jin Wook Kim, Yongin; Jee Hean Jeong, Suwon, all of (KR)

(73) Assignee: Doosan Corporation (KR)

(*) Notice: Subject to any disclaimer, the term of this patent is extended or adjusted under 35 U.S.C. 154(b) by 0 days.

(21) Appl. No.: 09/691,446

(22) Filed: Oct. 18, 2000

(51) Int. Cl.[7] .............................. A61K 7/00; A61K 7/48; A61K 9/127

(52) U.S. Cl. .................. 424/401; 424/450; 424/59; 514/844; 106/308

(58) Field of Search .................. 424/401, 450, 424/59; 106/308; 514/844

(56) References Cited

U.S. PATENT DOCUMENTS

| | | | |
|---|---|---|---|
| 4,622,074 A | * 11/1986 | Miyoshi et al. | 106/308 |
| 5,206,020 A | 4/1993 | Critchley et al. | 424/401 |
| 5,476,661 A | 12/1995 | Pillai et al. | 424/401 |
| 5,578,641 A | * 11/1996 | Jackson et al. | 424/401 |
| 5,627,056 A | 5/1997 | Casey et al. | 435/134 |
| 5,650,166 A | * 7/1997 | Ribier et al. | 424/450 |
| 5,662,912 A | 9/1997 | Moeller et al. | 424/401 |
| 5,792,794 A | 8/1998 | Lambers et al. | 514/559 |
| 5,840,940 A | 11/1998 | De Pater et al. | 554/61 |
| 5,882,665 A | 3/1999 | Meyers et al. | 424/401 |

OTHER PUBLICATIONS

Journal Appl. Cosmetology , Morganti, p ; Fabrizi, G ; James, B. (1999), 17(3), 86–93 PB: International Ediemme.*

* cited by examiner

*Primary Examiner*—Diana D Dash
*Assistant Examiner*—Mina Haghighatian
(74) *Attorney, Agent, or Firm*—Ladas & Parry

(57) ABSTRACT

Disclosed are compositions for skin care and their medicinal uses. The compositions are identical in lipid constituents and structural properties to that of human stratum corneum. They comprise the major constituents for the lipid lamellar of the stratum corneum, including ceramides, cholesterol and fatty acids, the major constituents for epidermal cell membranes, including phospholipids, and physiologically active substances, including phytosphingosine and its derivatives. Without causing side effects, the cream composition for skin care is of much better skin penetration and water-retention capacity than are conventional compositions comprised of ceramide and other components in forms different from those of human skin. In addition to providing inhibitory activity against skin microorganisms, the cream composition brings about an improvement in the wrinkle condition of the skin, so that it can be applied to cosmetics. Also, it can be used as a medicinal material for the therapeutic treatment of inflammation, such as thermic erythema caused by IR and/or UV light.

15 Claims, 3 Drawing Sheets

CREAM COMPOSITION FOR SKIN CARE

BACKGROUND OF THE INVENTION

1. Field of the invention

The present invention relates to a composition for skin care, which is identical in lipid composition and structural properties to intercellular lipid lamella of stratum corneum.

2. Description of the Prior Art

In terms of structure, the skin can be divided into dermis, epidermis, and stratum corneum in accordance with the differentiation of keratinocyte cells from a basal layer. Particularly, the stratum corneum, which is the outermost layer of the skin, is primarily responsible for protecting the skin from external physical and chemical damage as well as functioning as a barrier to prevent the loss of internal water.

Deeply understanding the structure of the skin and the physical and chemical properties of epidermal lipid constituents is indispensable for and helpful in developing skin applications for maintaining the skin in healthy condition.

Since dry skin is a cause of various dermatological troubles, to maintain skin's moisture balance is fundamental to skin care. Also, the skin is exposed to numerous microorganisms and the stratum corneum is known to have components which act to maintain normal bacterial flora on the skin.

Phospholipids, one of the important skin lipids constituting the lipid lamella bilayer, are quantitatively present in the basal layer. However, phospholipids are present in lower proportions in the lipids of more outer epidermal layers. On the other hand, ceramides become more plentiful in more outer layers, amounting to as much as 50% of the intercellular lipids in the outer protective layers of skin, stratum corneum.

It is generally accepted that ceramides play a particularly important role in preventing the loss of the water through the stratum corneum and restoring any damaged skin lipid barrier of the stratum corneum. It is also known that phytosphingosine, a ceramide precursor, is formed as a result of the degradation of the ceramides of the stratum corneum and functions as a primary microorganism barrier to inhibit the growth of microorganisms on the outermost layer of the skin and to reduce skin troubles. A reduction of the ceramide content in the stratum corneum brings about a decrease of phytosphingosine content, leading to skin troubles such as acne and atopic dermatitis and giving off offensive odors.

As various skin diseases, including atopic dermatitis, are reported to be attributed to abnormal changes in the stratum corneum lipid composition, there is a new tendency to develop products from combinations of ceramides, cholesterol and fatty acids in the dermatology and cosmetic fields.

For these reasons, extensive research is concentrated on the development of skin care products taking advantage of stratum corneum lipids and phytosphingosine. In order to exhibit sufficient physiological activity, these substances must penetrate through the stratum corneum to the deeper layers of skin, such as epidermis and dermis, composed of a larger proportion of phospholipids. To this end, lipid lamellar type products must be developed to have structures similar to those of the lipid lamellar of the stratum corneum.

However, since ceramides and phytosphingosines are hydrophobic materials, they are low in solubility and highly apt to form crystals. Therefore, ceramides and phytosphingosines are poor in stability in cosmetic formulations and limited in their applications. Recently, ceramide mixtures formed with the help of ethanol/propylene glycol have been reported to recover damaged skin to a normal condition, but it is also reported that their use for a long period of time makes the skin dry, and propylene glycol can so much as cause contact allergy. On account of, the use of solvents and additives unsuitable for use on the skin, the conventional skin care compositions cause side effects and show poor trans-epidermal penetration. In order to solve the above-mentioned problems, there have been developed pseudo-ceramide comprising products which are of high solubility and facile utility. However, pseudo-ceramides, which are not in natural form, may cause problems in that they are easily accumulated in the skin because they are not biodegradable. More importantly, pseudo-ceramides lack biological activities that the natural ceramides or phytosphingosine retain.

SUMMARY OF THE INVENTION

Therefore, a specific formulation is required in order to sufficiently exert the effects of ceramides and phytosphingosines on the skin. As a solution to these problems, the present inventors have developed a composition for skin care, which is superior in skin compatibility, that is, which is similar in composition and structural properties to that of human skin.

It is an object of the present invention to provide a skin care composition which is similar in composition and structural properties to that of human skin, thereby to sufficiently exert the efficacies of ceramides and phytosphingosine and a preparing method thereof.

The composition of the present invention comprises ceramides, cholesterol and fatty acids, which are major intercellular components of stratum corneum, phospholipids which are major components of epidermal cell membranes, and phytosphingosine and its derivatives, which serve as physiologically active materials.

The ceramides useful in the present invention comprise derivatives of sphingosine, sphinganine and phytosphingosine, and mixtures thereof.

Available in the present invention is phytosphingosine itself. Polar derivatives are, however, preferred in order to enhance the emulsification and solubility of phytosphingosine.

For example, organic acids are used to produce organic salts of phytosphingosine which are neutral in pH. Available organic acids are exemplified by hydrogen chloride, lactic acid, $\alpha$-, or $\beta$-hydroxy acid, and salicylic acid.

As the fatty acids in the skin care composition of the present invention, saturated or unsaturated fatty acids containing 10–25 carbon atoms or combinations thereof are used.

Functioning as a skin penetration enhancer and an emulsifier, phospholipids used in the present invention are preferably hydrogenated or hydroxylated to contribute to the stability of the composition.

DETAILED DESCRIPTION OF THE INVENTION

Figure 1:
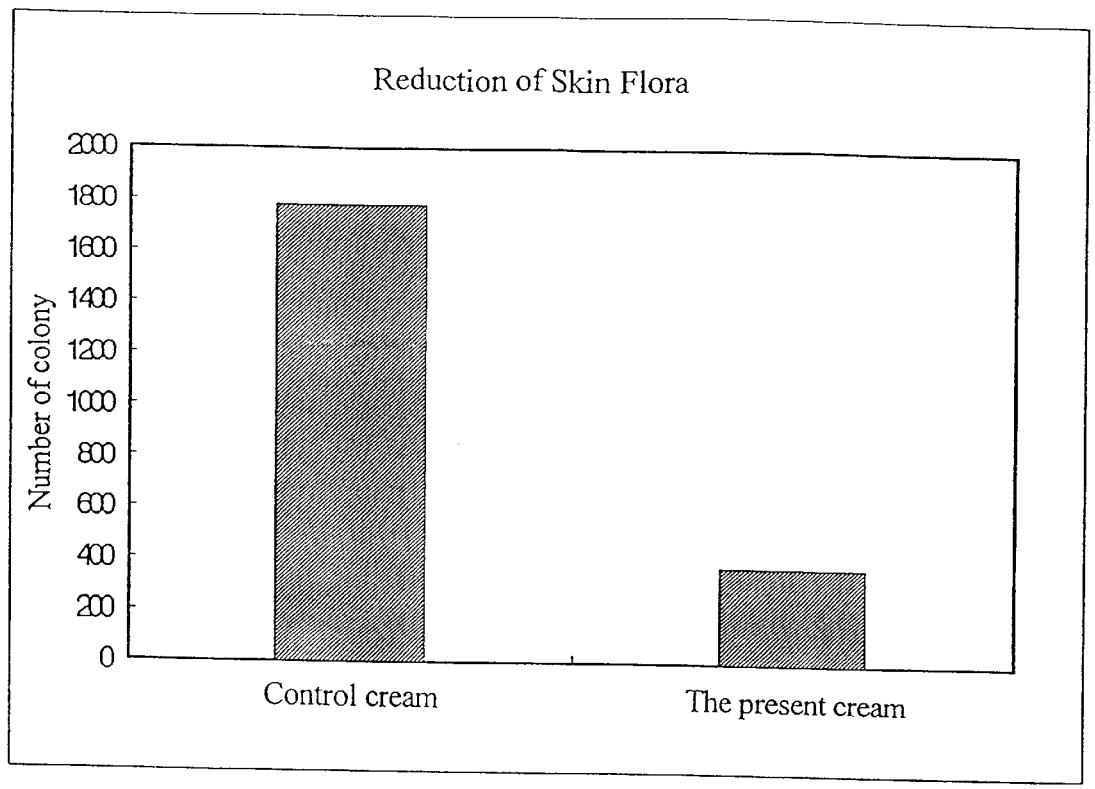
FIG. 1 is a graph showing the inhibitory effect of the cream composition of the present invention against the microorganisms that are present on the skin.

The present invention is directed to a cream composition for skin care, which is similar in composition and structural properties to that of human skin, thereby enabled to sufficiently exert the efficacies of ceramides and phytosphingosine and its derivatives and to a preparing method thereof.

The cream composition of the present invention comprises ceramides, cholesterol and fatty acids, which are major intercellular components of stratum corneum, phospholipids which are major components of epidermal cell membranes, and phytosphingosine and its derivatives, which serve as physiologically active materials.

In consideration of the reports revealing that the constituents of the lipid lamellar structure of the stratum corneum are concerned with various disorders of the skin, much research has been directed to the restoration of damaged skin by provision of the main constituents for the lipid lamella of the stratum corneum, that is, ceramides, cholesterol, and fatty acids.

When liquid crystals are formed with lipids of the stratum corneum to prepare the composition of the present invention, the best efficacy for skin care is found to be obtained from the weight ratio of 10:5:4 ceramides:cholesterol:fatty acids. In other words, the cream composition in which the constituents are formulated at said weight ratio most effectively promotes the restoration of a damaged skin barrier.

However, ceramides, known to play the most pivotal role among all the constituents for the formation of lipid lamellar structure of the stratum corneum, are hydrophobic and easily undergo crystallization, making it very difficult to develop products which meet stability, utility and penetration requirements all at once. In order to solve this problem, the present invention succeeded in developing oil-in-water type skin care compositions which are superior in skin compatibility and free of side effects by employing only natural materials found in human skin, with neither synthetic surfactants nor solvents.

The ceramides used in the present invention are amide derivatives in which fatty acids are attached to the amine groups of sphingosine, phytosphingosine, and sphinganine, exemplified by the following structural formulas:

Ceramide Derivatives Useful in the Present Invention

1. Sphingosine Derivatives $$CH_3(CH_2)_{12}-CH=CH-CH(OH)-CH(NH-CO-R)-CH_2OH$$

2. Sphinganine Derivatives $$CH_3(CH_2)_{14}-CH(OH)-CH(NH-CO-R)-CH_2OH$$

3. Phytosphingosine Derivatives $$CH_3(CH_2)_{13}-CH(OH)-CH(OH)-CH(NH-CO-R)-CH_2OH$$

wherein R is a $C_{6-25}$ unsaturated fatty acid which has one or two double bonds or a $C_{6-25}$ saturated fatty acid which has a hydroxy group at the $\alpha$ or $\beta$ position.

Preferably, to form a stable emulsion, the ceramide or its derivatives are used at an amount of 4–20 wt % based on the total weight of the composition.

The cholesterol used in the present invention is selected from the group consisting of cholesterol, cholesterol sulfate, cholesterol hemisuccinate and mixtures thereof. The presence of cholesterol is helpful in the liquid lamellar crystallization of ceramides, stabilizing the liquid crystals formed. Cholesterol is preferably used at an amount of 2–8 wt % based on the weight of the composition and most preferably at an amount of 40–50 wt % based on the weight of the ceramides used.

Useful in the present invention are saturated fatty acids containing 6–25 carbon atoms, unsaturated fatty acids containing 6–25 carbon atoms with one or two double bonds, or combinations thereof. They are most preferably used at an amount of 2–8 wt % based on the weight of the composition.

When liquid crystals are formed with lipids of the stratum corneum to prepare the composition of the present invention, the best efficacy for skin care is found to be obtained from the weight ratio of 10:5:4 ceramides:cholesterol:fatty acids. In other words, the cream composition in which the constituents are formulated at said weight ratio most effectively promotes the restoration of any damaged skin barrier.

In the present invention, phytosphingosine may be used 1) as it is or in an organic acid-modified form, for example, 2) a phytosphingosine organic salt or 3) an electrically charged derivative in order to improve its emulsification capability and solubility.

Even if present at an amount of as low as 1 wt % in the lipid lamellar of the stratum corneum, phytosphingosine is very important because of its antimicrobial activity. Therefore, it makes a contribution to the maintenance of the skin in normal, healthy conditions. In addition, phytosphingosine is a precursor for ceramide, serving as a physiologically active material. It was found to show good therapeutic efficacy when tested on patients suffering from acne.

Phospholipids, important constituents of cell membranes, are extensively studied for drug delivery systems owing to their tendency to form lipid bilayer structures and liposomes in water. In addition, phospholipids play a role as a skin penetration enhancer and a skin softener.

In terms of oxidative stability, the phospholipids that are hydrogenated or hydroxylated with an iodine value of around 20 are preferred.

The skin care compositions of the present invention form vehicles which can entrap the materials beneficial to the skin, so that the skin care compositions can be used as pre-formulators of skin care products where therapeutic reagents are utilized.

A better understanding of the present invention may be obtained in light of the following examples which are set forth to illustrate, but are not to be construed to limit the present invention.

Preparation Example I

Preparation of Organic Salts of Phytosphingosine

Phytosphingosine was dissolved in ethanol, then an equal equivalent of an organic acid was added. After being stirred at room temperature for 30 min, the solution was deprived of ethanol under a reduced pressure and added with acetone to precipitate. The precipitate was filtered and dried (Yield: 98%).

Preparation Example II

Preparation of Cream Composition for Skin Care

The cream composition for skin care was prepared by slowly adding an aqueous phase in a lipid phase with stirring after the two phases were separately formed.

For the lipid phase, first, 1 g of stearic acid and 2.5 g of cholesterol were added to 5 g of tricarproid and the mixture was heated up to 80° C. After completion of the dissolution of the mixture, the solution was added with 5 g of ceramide and stirred to thorough dissolution. Subsequently, 2 g of lecithin was added and dissolved, followed by adding 1.5 g of oleic acid and 0.5 g of linoleic acid.

For the aqueous phase, 80 g of distilled water was heated up to 80 ° C., after which 1 g of phytosphingosine-HCl was added thereto. Then, 1 g of phytosphingosine and 1 g of lactic acid were added, followed by stirring to complete dissolution. The aqueous phase was slowly added in the lipid phase with stirring at 80° C. for 60 min and then, slowly cooled to room temperature to afford a creamy composition.

Test Example I

Antimicrobial Activity Against Microorganisms Inhabiting on Skin

The cream composition prepared in Example 2 was tested for antimicrobial activity against the microorganisms on the skin as follows: To one side of the face of each of ten test subjects was applied the cream composition. After 2 hours, an examination was made of the microorganism distribution on each side of each subject's face. In this regard, each of two sides of the subjects' faces was scraped with two sterilized cotton balls, respectively and each of the cotton balls was put in sterile distilled water that was then vigorously stirred for 3 min. 100 □l of each solution was smeared over a tryptic soy agar medium that was then incubated at 37° C. for 24 hours. The number of the colonies formed was counted.

Taken from the ten subjects, the results for the antimicobial activity of the cream composition are given in Table 1, below. The inhibitory activity against skin microorganisms of the cream composition of the present invention is also shown in FIG. 1. The numbers in FIG. 1 are the arithmetic means of the total number of the colonies obtained from the opposite sides of the face in each of 10 test subjects.

TABLE 1

Inhibitory Activity Against Epidermal Microorganisms

| Test Subject No. | Tested Side | Untreated Side | % Reduction |
| --- | --- | --- | --- |
| 1 | 126 | 1,328 | 90% |
| 2 | 268 | 584 | 54% |
| 3 | 189 | 249 | 24% |
| 4 | 0 | 0 | 0% |
| 5 | 520 | 2,056 | 75% |
| 6 | 208 | 2,136 | 90% |
| 7 | 110 | 1,056 | 90% |
| 8 | 372 | 3,680 | 90% |
| 9 | 386 | 580 | 33% |
| 10 | 320 | 3,891 | 92% |

Test Example 2

Anti-Wrinkling Effect

A cream containing 5 wt % of the cream composition of the present invention was applied to one area of crow's feet wrinkles of each of seven female volunteers 44 to 53 years old, two times a day, for example, in the morning and evening, for 28 days with an application of a control to the other area of crow's feet wrinkles. After completion of the application, the wrinkles in the areas were examined for the change in number, depth, and total area with the aid of a skin image analyzer. Measurements were made separately according to the degreed wrinkling, that is, the relative amounts of fine wrinkles, moderate wrinkles and deep wrinkles on an area of 1 cm².

The result data for each particular, obtained through the skin image analyzer, was substituted into the following equation to represent the anti-wrinkling effect of the cream composition in wrinkle reduction percentage.

$$(R\ \%) = \frac{(TCE\ D28 - TCE\ DO) - (TCE\ D28 - TCE\ DO)}{TCO\ D28 - TCO\ DO + TCE\ DO} \times 100$$

wherein TCE=treated with the cream according to the present invention

TDO=treated with a control cream

DO=before application of cream

D28=28 days after application of cream

Figure 2:
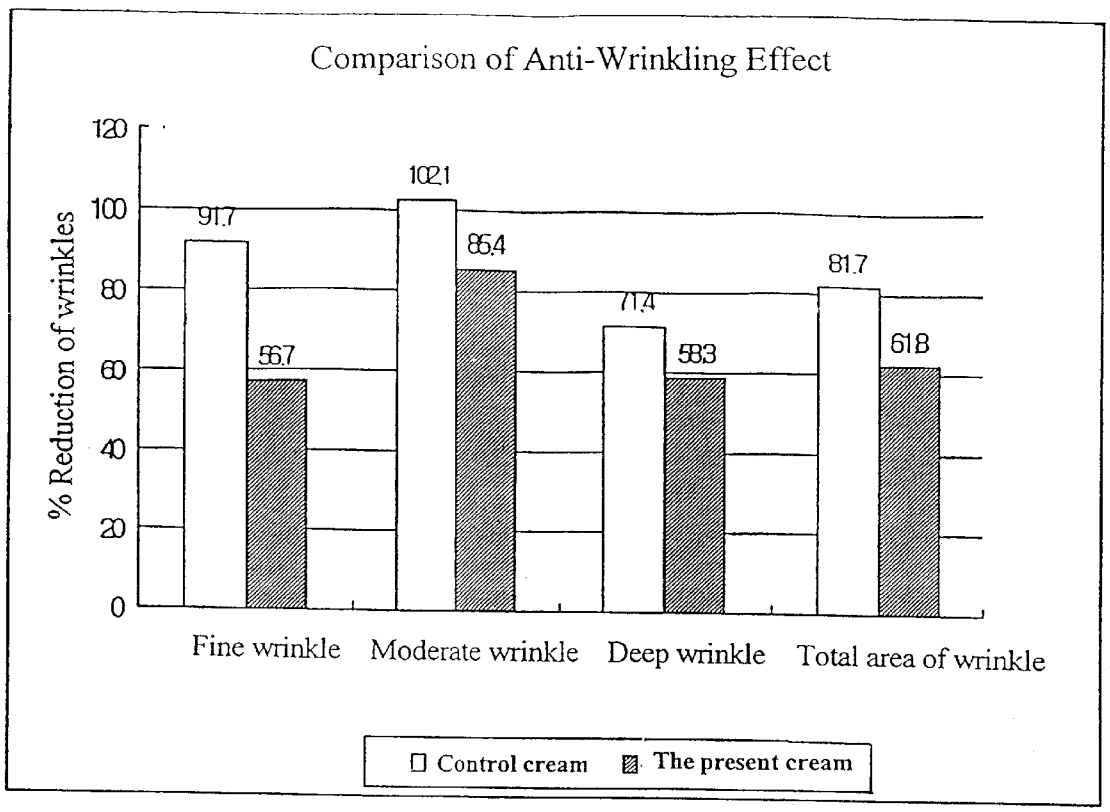
FIG. 2 is a graph showing the inhibition effect of the cream composition against wrinkling of the skin.

With reference to FIG. 2, there is a histogram that shows the difference in anti-wrinkle effect between the cream of the present invention and a conventional cream after their application for 28 days. As clearly shown in the histogram, significant reductions were brought about in the numbers of all of the fine, moderate and deep wrinkles by the application of the cream composition according to the present invention. Particularly, the fine wrinkles in the vicinity of the crow's feet were most greatly improved. The total number of wrinkles in the tested areas was reduced.

Test Example 3

Anti-Inflammatory Effect

When the cream composition of the present invention was used, the anti-inflammatory effect that consumers could benefit from was tested through in vivo experiments. For comparison, a commercially available lotion cream was used as a control. The alleviating effect of the cream composition was examined against inflammations of the skin, such as thermic erythema and actinic erythema, which are usually caused by excessive exposure to infra-red light and ultraviolet light, respectively. The test was separately conducted in two panel groups: one consisting of seven women 22–59 years old and the other of one man and six women 18–29 years old.

The alleviating effect of phytosphingosine against inflammation was expressed by the digitization of the measurements for cutaneous microcirculation, erythema color and dermal temperature. The measurement of the cutaneous microcirculation was achieved by means of Hematron, a thermal conduction meter, which takes advantage of the phenomenon that thermal conductivity increases and decreases according to the contraction and expansion of capillary vessels, respectively. The alleviation of inflammation may be indexed by the swelling subsidence resulting from the contraction of expanded capillary vessels. For the measurement of erythema color, a Minolta CR300 chromameter was used. Hematron was also used for the measurement of dermal temperature.

Figure 3:
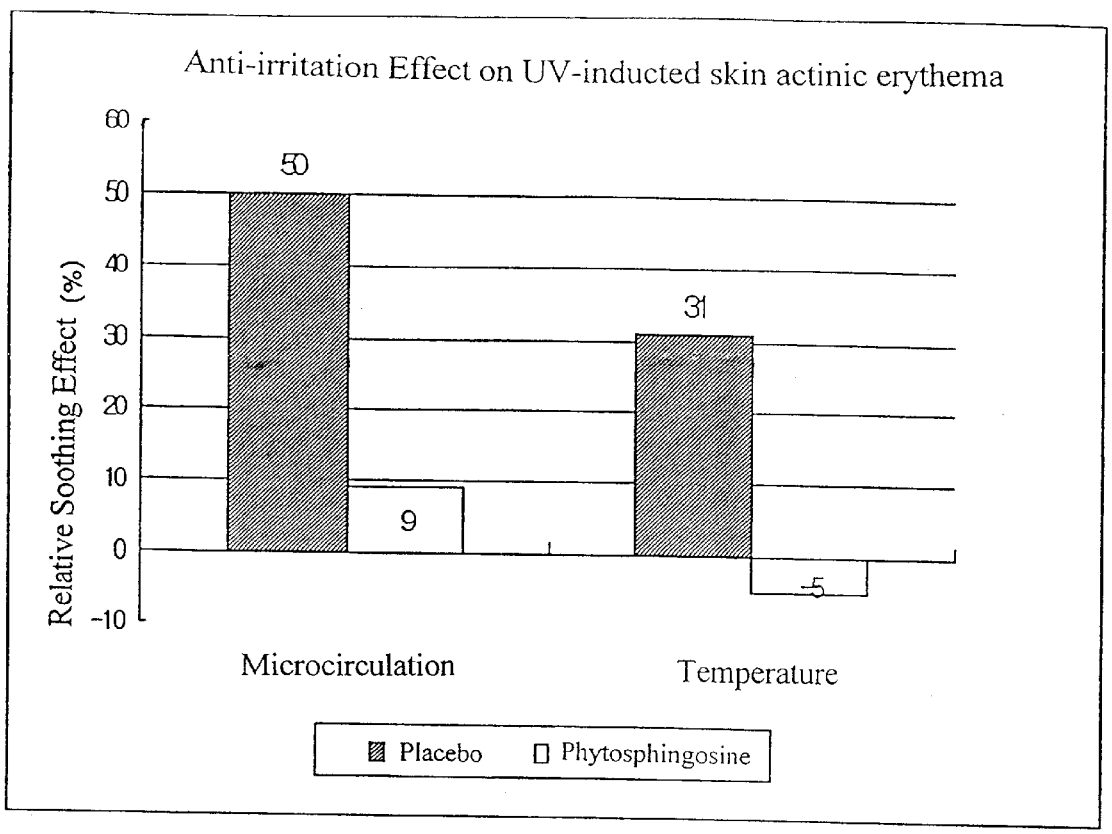
FIG. 3 is a graph showing the alleviating effect of the cream composition against the erythema caused by UV light.

Using as a source of radiation an IR light irradiation apparatus, such as IR Philips 250S, the test subjects were irradiated with an irradiation intensity of 70 mW/cm$^2$ for 30 min at a distance of 50 cm from the source, so as to cause thermic erytherma. The irradiated area was 14 cm$^2$. Using as a source of UV radiation, an apparatus equipped with a xenon lamp, such as Suntest/Original Hanau, the test subjects were irradiated at an intensity of 100 W on an area of 4 cm$^2$. The irradiation with IR and UV was conducted after the determination of minimal erythemal doses (MED) for each individual subject. Measurements were made of the alleviating effect of the cream composition of the present invention on the fifth and the seventh day after the UV irradiation. The results are given in FIG. 3.

1. Alleviating Effect on Thermic Erythema

Compared with the placebo control cream, the cream composition of the present invention is of better alleviating activity against inflammation as recognized from the fact that a decrease in cutaneous microcirculation obtained from the cream composition of the present invention was seen in over 80% of the test subjects in a range from −0.12 mW/cm≡° C. to −0.72 mW/cm≡° C. For reference, it is accepted that a thermal conductivity difference ($\Delta T$) of not less than −0.1 mW/cm≡° C. would be reliable. In addition, over 60% of the test subjects were found to have experienced the thermic erythema at a lesser frequency as measured by the Chromameter.

2. Alleviating Effect on UV-Caused Erythema

Compared with the placebo control cream, the cream composition of the present invention is better in alleviating activity against inflammation as recognized from the fact that a decrease in cutaneous microcirculation obtained from the cream composition of the present invention was seen in over 60% of the testees in a range from −0.10 mW/cm=° C. to −0.70 mW/cm≡° C. For reference, it is accepted that a thermal conductivity difference ($\Delta T$) of not less than −0.1 mW/cm≡° C. would be reliable. In addition, the dermal temperature on the stimulated (irradiated) area was found to be significantly reduced in over 60% of the testees as measured by Hematron. By individual, the dermal temperature reduction ranged from −0.7 to −1.1° C. This also showed the alleviating effect of the cream composition of the present invention on the inflammation caused by UV irradiation.

Without causing side effects, as described hereinbefore, the cream composition for skin care according to the present invention is of much better skin penetration and water-retention capacity than are conventional compositions comprised of ceramide and other components in different forms from those of natural epidermal membranes. In addition to providing inhibitory activity against skin microorganisms, the cream composition of the present invention is more effective for the treatment of wrinkles of the skin, so that it can be applied to cosmetics. Also, it can be used as a medicinal material for the therapeutic treatment of inflammation, such as the thermic erythema caused by IR and/or UV light.

What is claimed is:

1. A composition for skin care consisting essentially of the following components: ceramides, cholesterol, fatty acids, phospholipids, and phytosphingosine or an organic salt of phytosphingosine, said components being present in the composition in respective amounts effective to form the composition as a stable emulsion and to provide the composition with antimicrobial activity.

2. The cream composition as set forth in claim 1, wherein the ceramides are present in an amount of 4–20 weight % based on the total weight of the composition.

3. The cream composition as set forth in claim 1, wherein the cholesterol is present in an amount of 2–8 weight % based on the total weight of the composition.

4. The cream composition as set forth in claim 1, wherein the fatty acids are present in an amount of 2–8 weight % based on the total weight of the composition.

5. The cream composition as set forth in claim 1, wherein the fatty acids are saturated fatty acids containing 6–25 carbon atoms, unsaturated fatty acids containing 6–25 carbon atoms with one or two double bonds, or combinations thereof.

6. The cream composition as set forth in claim 1, wherein the cholesterol is selected from the group consisting of cholesterol sulfate, cholesterol hemisuccinate and mixtures thereof.

7. The cream composition as set forth in claim 1, wherein the phospholipids are hydrogenated or hydroxylated with an iodine value of around 20.

8. The composition of claim 1, wherein the phytosphingosine is present in the composition in a natural form.

9. The composition of claim 1, wherein the organic salt of phytosphingosine is present in the composition.

10. The composition of claim 9, wherein the ceramides are present in an amount of 4–20 weight % based on the total weight of the composition, the cholesterol is present in an amount of 2–8 weight % based on the total weight of the composition, and the fatty acids are present in an amount of 2–8 weight % based on the total weight of the composition.

11. The composition of claim 10, wherein the phospholipids are hydrogenated or hydroxylated.

12. The composition of claim 11, wherein the fatty acids are saturated fatty acids containing 6–25 carbon atoms, unsaturated fatty acids containing 6–25 carbon atoms with one or two double bonds, or a combination thereof.

13. A method for treating wrinkles on the skin of a user comprising:
   a) providing the composition of claim 1; and
   b) applying the composition to the skin of the user in an amount effective to treat the wrinkles.

14. A method for treating inflammation of the skin of a user comprising:
   a) providing the composition of claim 1; and
   b) applying the composition to the skin of the user in an amount effective to effect a therapeutic treatment of the inflammation.

15. The method according to claim 13, wherein the inflammation is erythema caused by IR or UV light or both.

* * * * *